US00PP09971P

United States Patent [19]

Hofmann

[11] Patent Number: Plant 9,971

[45] Date of Patent: Jul. 15, 1997

[54] VARIETY OF GERANIUM NAMED 'NORTH STAR'

[75] Inventor: Christa Hofmann, Grossdittmannsdorf, Germany

[73] Assignee: Elsner Pac Jungpflanzen, Germany

[21] Appl. No.: 536,703

[22] Filed: Sep. 29, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,312 10/1984 Hoffmann ..... Plt./87.12

P.P. 8,894 9/1994 Klemm .

*Primary Examiner*—James R. Feyrer

*Attorney, Agent, or Firm*—Webb Ziesenheim Bruening Logsdon Orkin & Hanson, P.C.

[57] ABSTRACT

The new cultivar is a early, rich flowering mass-production variety. It is not sensitive to chlorosis and has high productivity on the motherplant. Its elegant pure white flowers have big umbels and continuously flower. Its good garden performance is shown by its very good resistance to rainfall and bad weather. It does not change from the white color to light pink under unfavorable climatic conditions and does not display a neck break. It also has a vigorous compact mound growth. The new cultivar is an improvement in comparison to the old white variety "PAC Aphrodite".

1 Drawing Sheet

BACKGROUND OF THE INVENTION

The present invention comprises a new and distinct cultivar of *Pelargonium×hortorum* known by the varietal name 'North Star'. The new variety was discovered at Elsner pac Jungpflanzen in Dresden, Germany in April, 1990. The new variety was discovered by crossbreeding several breeding lines, which are unnamed, but which are maintained proprietary for breeding purposes. The new variety was first asexually reproduced by cuttings at Elsner pac Jungpflanzen in Dresden, Germany in September, 1990. It has also been trial and field tested from the year after discovery up to now at Elsner pac Jungpflanzen in Dresden, Germany and has been found to retain its distinctive characteristics through successive propagations.

The plant history was taken on six week plants blossomed under the natural light in a green house in 12 cm pots. The cultivar when grown in a glass greenhouse was potted on the Feb. 17, 1995 and flowered on Mar. 30, 1995.

DESCRIPTION OF THE DRAWING

The accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Elsner pac Jungpflanzen in Dresden, Germany. The plant history was taken on six week plants blossomed under natural light in a greenhouse and the color readings were taken indoors under natural light in a room near a window without direct sunlight. Color references are primarily to The R.H.S. Color Chart of The royal Horticultural Society of London.

THE PLANT

Classification:

*Botanical.*—*Pelargonium×hortorum.*

*Commercial.*—Commercial florists' geranium.

*Form.*—Compact mound form.

*Height.*—18.0–20.0 cm.

*Growth.*—Free and early flowering, basel branching.

*Strength.*—Stands upright without artificial support. More tolerant than other plants of this market class to the vagaries of weather.

*Foliage.*—Stalked leaf attachment, no zone present.

Leaves:

*Size.*—Length: 5.0–6.0 cm. Width: 9.0–11.0 cm.

*Shape.*—Reniform, cordate base.

*Margin.*—Crenate.

*Texture.*—Pubescent.

*Color.*—Top: Green Group 137B. Bottom: Green Group 138B.

Zonation:

*Degree.*—slight.

*Color.*—137A.

Ribs and veins:

*Venation type.*—Palmate.

*Color.*—Green Group 138B.

Petioles:

*Color.*—Green Group 137C.

*Length.*—4.0–5.0 cm.

Stem:

*Color.*—Yellow-Green Group 145A.

*Internodes.*—2.5–4.0 cm in length.

THE BUD

Shape: Upright hemispherical clusters.

Size (diameter): 3.0 cm.

INFLORESCENCE

Blooming habit: Free and early flowering, semi-double, not shattering.

Size (diameter): 12.0–15.0 cm, fully open bloom.

Borne: Umbel, florets on pedicel, pedicel on peduncle, flowers above the foliage.

Umbels:

*Number.*—10.

*Number of florets per umbel.*—12.

*Size.*—5.0 cm in diameter.

Florets:

*Form.*—Semi-double, flat to slightly cupped.

*Color.*—Top: White Group 155A. Bottom: White Group 155A.

Petals:

*Shape.*—6–8, close together, ovate.

*Margin.*—Entire.

*Texture.*—Smooth.

*Size.*—2.8 cm long, 2.2 cm wide.

*Texture and appearance.*—Petals are smooth, slightly reflective, and present a starkly contrasting and dramatically attractive white color splash above the medium green leaves.

*Effect of heat and sun.*—Petals to not oxidize in summer heat and direct sun. Petals are spent by the plant.

Petaloids:

*Size.*—2.0 cm long, 0.4 cm wide.

*Quantity.*—2–3.

*Shape.*—Single based, with ends split to 1–3 points, points twisted.

*Color.*—Like the petals.

Calyx:

*Form.*—Cup-shaped.

*Color of sepals.*—Yellow Green Group R.H.S. 145A.

*Size of sepals.*—1.0 cm long, 0.4 cm wide.

Pedicel:

*Length.*—2.0 cm.

*Color.*—Yellow-Green Group 145A.

Peduncle:

*Color.*—Yellow-Green Group 146B.

*Length.*—15.0–18.0 cm.

Disease resistance: Apparently highly resistant to common diseases of plants of this market class because no unusual susceptibilities have been observed in the culture of this plant.

Lasting quality: Good.

REPRODUCTIVE ORGANS

Stamens:

*Number.*—7–9.

*Anthers.*—2.0 mm in length.

*Filaments.*—Length: 8.0 mm. Color: White.

*Pollen.*—Golden brown.

Pistils:

*Number.*—1.

*Length.*—10.0 mm.

*Stigma.*—Number: 1, 5–6 parted. Color: White.

*Style.*—Length: 5.0 mm. Color: Pale Green.

Ovaries:

*Pubescence.*—Superior, pubescent.

*Length.*—5.0 mm.

*Width.*—3.0 mm.

*Color.*—Green.

*Fecundity.*—Pollen is formed. No seed setting during normal growing as balcony and bedding plant. Seed setting observed after hard pollination.

Seed formation: None during normal growing.

Fruit: None observed.

GENERAL CHARACTERISTICS

1. New semi-double pure white color.
2. Medium green foliage not sensitive to chlorosis.
3. Early, rich flowering, mass-production variety.
4. High productivity on the motherplant.
5. Elegant flowers, big umbels and continuous flowering.
6. Good garden performance.
7. Very good resistance to rainfall and bad weather.
8. No neck break and no change of the white color to light pink under unfavorable climatic conditions.
9. Vigorous compact mound growth.
10. Essential improvement in comparison to the old white variety "PAC Aphrodite".

I claim:

1. A new and distinct variety of geranium plant substantially as shown and described.

* * * * *

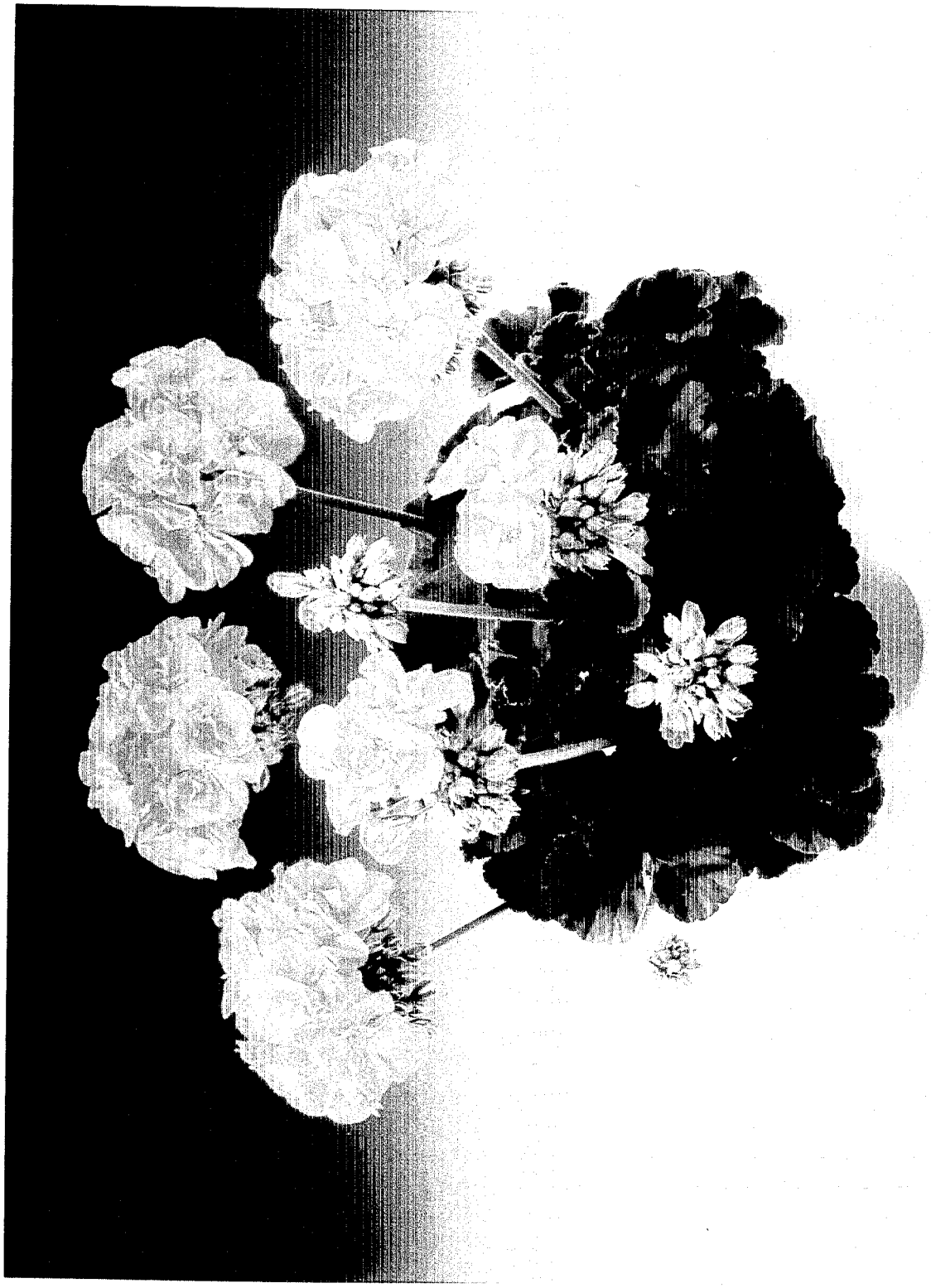

UNITED STATES PATENT AND TRADEMARK OFFICE

CERTIFICATE OF CORRECTION

PATENT NO. : Plant 9,971

DATED : July 15, 1997

INVENTOR(S) : Christa Hofmann

It is certified that error appears in the above-identified patent and that said Letters Patent is hereby corrected as shown below:

The drawing in Patent No. Plant 9,971 should be in Patent No. Plant 9,970.

The drawing in Patent No. Plant 9,970 should be in Patent No. Plant 9,971.

Signed and Sealed this

Thirteenth Day of January, 1998

Bruce Lehman

*Attest:*

BRUCE LEHMAN

*Attesting Officer*

*Commissioner of Patents and Trademarks*